United States Patent [19]
Eckhof et al.

[11] Patent Number: 5,902,303
[45] Date of Patent: May 11, 1999

[54] PIN-TYPE HOLDING ELEMENT FOR AN ORTHOPAEDIC HOLDING SYSTEM

[75] Inventors: Stephan Eckhof, Tuttlingen; Karl-Ernst Kienzle, Immendingen; Lino Taddia, Wurmlingen; Rudolf Zepf, Rietheim-Weilheim, all of Germany

[73] Assignee: Aesculap AG & Co. KG, Tuttlingen, Germany

[21] Appl. No.: 09/008,165

[22] Filed: Jan. 16, 1998

[30] Foreign Application Priority Data

Jan. 23, 1997 [DE] Germany ............... 197 02 201

[51] Int. Cl.$^6$ ..................................... A61B 17/59
[52] U.S. Cl. .................. 606/60; 606/61; 606/62; 606/73
[58] Field of Search ............... 606/60, 61, 62, 606/63, 64, 73, 70, 71, 72

[56] References Cited

U.S. PATENT DOCUMENTS

| | | | |
|---|---|---|---|
| 5,176,709 | 1/1993 | Branemark | 606/62 |
| 5,501,684 | 3/1996 | Schlapfer et al. | |
| 5,713,900 | 2/1998 | Benzel et al. | 606/60 |
| 5,735,853 | 4/1998 | Olerud | 606/69 |

FOREIGN PATENT DOCUMENTS

| | | |
|---|---|---|
| 0 201 024 | 11/1986 | European Pat. Off. |
| 39 12 703 | 10/1990 | Germany |
| 672 245 | 11/1989 | Switzerland |

*Primary Examiner*—Michael Buiz
*Assistant Examiner*—Jackie Tan-Uyen Ho
*Attorney, Agent, or Firm*—Barry R. Lipsitz; Ralph F. Hoppin

[57] ABSTRACT

In order to connect the core undetachably to the holding element in the case of a pin-type holding element for an orthopaedic holding system with an elastically compressible, head-shaped widened portion and with a central opening, into which a core may be inserted, which prevents an elastic compression of the head-shaped widened portion by filling out the central opening in the region of the widened portion without expanding this, it is proposed that the core is displaceable in the opening between a locking position, in which it fills out the central opening in the region of the widened portion, and a release position plunging deeper into the central opening, in which it releases the central opening in the region of the widened portion and thus allows its elastic compression

16 Claims, 2 Drawing Sheets

PIN-TYPE HOLDING ELEMENT FOR AN ORTHOPAEDIC HOLDING SYSTEM

BACKGROUND OF THE INVENTION

The invention relates to a pin-type holding element for an orthopaedic holding system with an elastically compressible, head-shaped widened portion and with a central opening, into which a core may be inserted, which prevents an elastic compression of the head-shaped widened portion by filling out the central opening in the region of the widened portion without expanding this.

Such a pin-type holding element is proposed in the German patent application 195 45 612.2-35. It is used, for example, for fixing bone plates to bones, the holding elements in this case being constructed as bone screws. These bone screws are inserted into openings in the bone plate, the edge of which is undercut, i.e. the diameter of the edge is larger in the centre than on the top and bottom of the bone plate As a result, the head-shaped widened portion, which is constructed in the form of a spherical ring in the known case, is held in the opening of the bone plate so as to be undetachable in axial direction, but be able to rotate and swivel freely.

A holding pin is described in WO95/35067, the cylindrical widened portion of which is held in a similar manner in a spherical ring, which is in turn mounted in an opening of a bone plate so as to be able to rotate and swivel freely.

If such a holding pin, which may be inserted into a bone plate or into a bearing ring through elastic compression, is to be secured axially in this position, it has been proposed in the German patent application to prevent the elastic compression of the head-shaped widened portion through a core, which is inserted into a central opening of the pin-type holding element and fills out this central opening in the region of the widened portion in such a way that the parts of the head-shaped widened portion can no longer be moved elastically radially inwards If such a connection is to be released again, it is necessary to remove the core from the central opening. This is obstructive in an operation, since the holding element is then divided into two parts, one part of which has to be removed from the operating area.

SUMMARY OF THE INVENTION

The object of the invention is to construct a pin-type holding element of the aforementioned type so that it is possible, without removal of the core, to detach the connection of the holding element in the region of the head-shaped widened portion.

The object is achieved according to the invention in a holding element of the above-described type in that the core is displaceable in the opening between a locking position, in which it fills out the central opening in the region of the widened portion, and a release position plunging deeper into the central opening, in which it releases the central opening in the region of the widened portion and thus allows its elastic compression.

Therefore, for the solution the core is not pulled out of the holding element and removed, but on the contrary is pushed deeper into the central opening, which is constructed longer for this purpose, so that it can receive the more deeply inserted core. The insertion depth is so great in this case that the core is removed from the region of the widened portion, and as a result the parts of the widened portion can be moved elastically radially inwards again, so that release of the connection between the head-shaped widened portion, on the one hand, and the surrounding opening of the bone plate or surrounding bearing ring, on the other, is possible.

In principle, it is possible to displace the core in the central opening upwards again into the locking position Therefore, the core forms a locking device, which is mounted so as to be undetachable in the central opening of the holding element and displaceable in longitudinal direction, and can be displaced between two end positions.

It is favourable in this case if the core can be fixed in the central opening in the locking position against a displacement along the central opening, so that it does not unintentionally leave the locking position.

For example, the core can be fixed in the locking position in the central opening by an elastic catch connection.

It is advantageous in this case if the catch connection can be released by overcoming a releasing force, so that the displacement of the core into the release position is possible if a specific insertion force is overcome.

It is advantageous in this case if the catch connection can only be released in the direction towards being inserted more deeply, i.e. only in the case of a displacement towards the release position. As a result of this, the core cannot be drawn fully out of the holding element from the locking position, and therefore separation of the two parts is not possible.

In a preferred embodiment, it is provided that the core bears a catch which may be pressed in elastically in radial direction and locks into a catch recess in the wall of the central opening.

The catch can bear a slide-on surface on the side directed into the central opening, so that when the core is inserted into the release position, the catch is pressed radially inwards and is lifted out of the catch recess.

Moreover, it may be provided that the catch abuts against a stop, when the core is located in the locking position so that the core cannot be removed from the holding element via the locking position.

It is particularly favourable if at the lower end of the core two opposing elastic arms are arranged in extension of the core bearing the catches on their free end.

The catches can be triangular in particular in cross-section with a stop surface running transversely to the displacement direction on the upper end, an internal boundary running perpendicular thereto and with a slide-on surface directed radially outwards and sloping upwards from below.

It is advantageous if the catch recess is also triangular in cross-section with an upper stop surface running transversely to the longitudinal direction of the central opening and with a lower boundary running parallel to the slide-on surface of the catches.

In particular, the catch recess can be constructed as an annular groove in the inside wall of the central opening. To be able to displace the core out of the release position into the locking position again when necessary, it is provided in a preferred embodiment that the core has a mounting for a pulling device on its upper side.

For example, the mounting can be constructed as an internal threaded bore, into which a pulling member can be screwed.

While it is possible, in principle, to construct the central opening as a through hole, according to a preferred embodiment the central opening is constructed as a blind hole to receive the core in it so as to be closed on all sides.

The elastically deformable widened portion can be received in the described manner directly in an opening of a bone plate or a similar implant, which has a larger diameter in the centre than on the upper side and the lower side of the bone plate so that the widened portion, which is shaped like a spherical ring, for example, on the outside, is axially captive in the opening, but is accommodated so that it may be freely rotated and swivelled.

In another embodiment it is provided that the widened portion is held in a ring, which is mounted in an opening of the bone plate with an edge rebounding in the centre with respect to the upper side and the lower side so that it is axially undetachable and may be freely rotated and swivelled, and that the edge of the opening is narrowed on the upper or on the lower side only after the ring is inserted into the opening by deformation in relation to the centre of the opening.

In the first case, the holding element can be locked into the opening with the elastically compressible widened portion simply by a corresponding deformation of this widened portion, in the second case, however, the ring, which is not elastically compressible, must firstly be inserted into the bone plate. Since the opening receiving the ring is undercut, it is necessary to construct this opening on the insertion side firstly with a larger inside diameter so that the ring can be inserted. As soon as the ring is inserted, the diameter of the receiving opening at the insertion side is reduced, and this can be achieved by a corresponding deformation of the material, in which the receiving opening is arranged. This deformation can be achieved by a suitable tool, by heating etc. in the case of thermoplastic materials.

The holding element is then locked into the ring inserted in this manner into an opening of an implant, said ring being mounted in this opening so that it can be freely rotated and swivelled, while being undetachable, and this is achieved by elastic compression of the widened portion of the holding element, for example, the holding element can have a circumferential rib for this purpose which snaps into a corresponding complementary circumferential groove of the bearing ring.

The following description of preferred embodiments of the invention serves for more detailed explanation in association with the drawing.

DETAILED DESCRIPTION OF THE INVENTION

The holding element according to the invention is explained by the example of a bone screw 1, which is inserted into an opening 2 of a bone plate 3.

Figure 1:
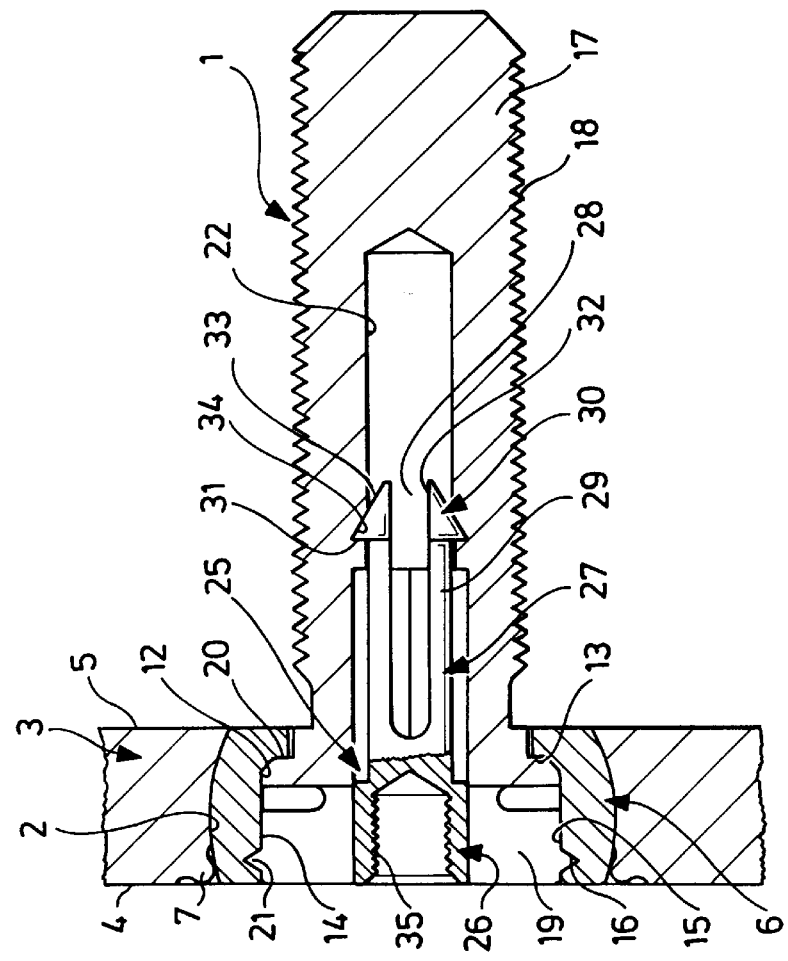
FIG. 1 is a view in longitudinal section of a holding pin inserted into a bone plate by means of a bearing ring, with the core in the locking position.

The opening 2 of the bone plate 3 has an undercut edge, i.e. in the centre of the bone plate 3 the diameter of the opening 2 is larger than on the upper side 4 or on the lower side 5. The cross-section of the opening 2 can be spherical, for example, as is evident from the example in FIG. 1.

Figure 2:
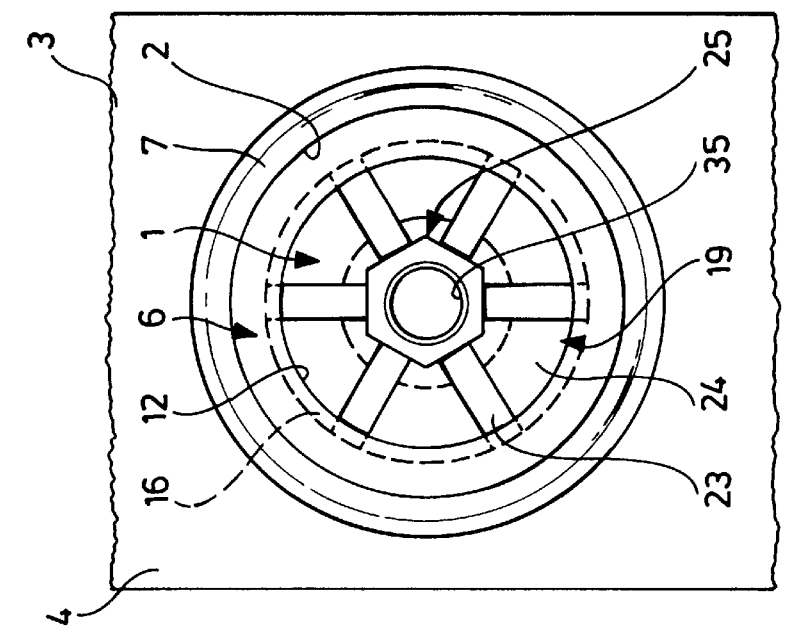
FIG. 2 is a top view onto the holding element of FIG. 1 inserted into a bone plate.
Figure 3:
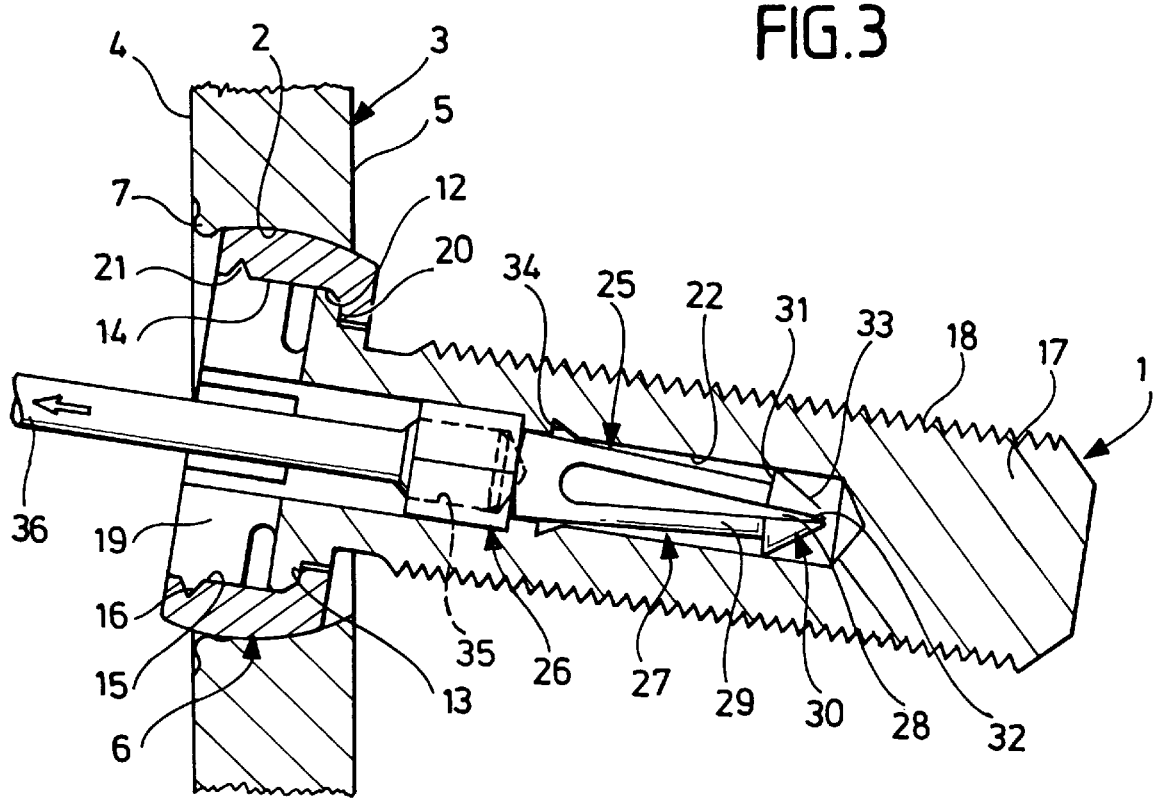
FIG. 3 is a view similar to FIG. 1 with the core in the release position with a pulling member connected to the core.

A bearing ring 6, which is of spherical shape on the outside, is inserted into this opening 2 with the undercut edge, said bearing ring being held in the opening 2 so that it is rotatable around its longitudinal axis and may be swivelled relative to the plane of the bone plate 3. For insertion of the bearing ring 6, the opening 2 is constructed in the bone plate 3 so that it has a reduced diameter only on one side, and on the opposite side, i.e. the insertion side of the bearing ring 6, the diameter is firstly as large as the larger diameter of the opening 2 in the centre of the bone plate. As a result, the bearing ring 6 can be inserted directly into the opening 2 from with this side. After the insertion, the bone plate 3 is deformed at the edge in the region of the opening 2 in such a way that the diameter of the opening 2 is also reduced on the insertion side, so that the bearing ring 6 is fixed in the opening 2. This deformation can be achieved, for example, by a stamping tool or by heating when using a thermoplastic material. The deformed edge 7 is shown schematically in the representation in FIG. 1. In the embodiment shown in FIGS. 1 to 3, the bearing ring 6 may be swivelled in the opening 2 over an angle of almost any desired size. Since this is not generally necessary, it is possible to provide stops for this swivelling movement This is realised in the embodiment of FIG. 4, which is otherwise of the same construction and in which the same parts therefore have the same reference numerals. In this embodiment, the bearing ring 6 has two circumferential ribs 8 on its outer surface, which abut against the spherical ring-shaped inside wall 9 of the opening 2. This inside wall 9 is defined at the upper side 4 and the lower side 5 of the bone plate 3 by a projecting step 10 or 11. At least one of these steps can be produced in the described manner by a deformation of the bone plate material.

The circumferential ribs 8 abut against these two steps upon a swivelling movement of the bearing ring 6 in the opening 2, and as a result the swivelling angle is restricted.

Figure 4:
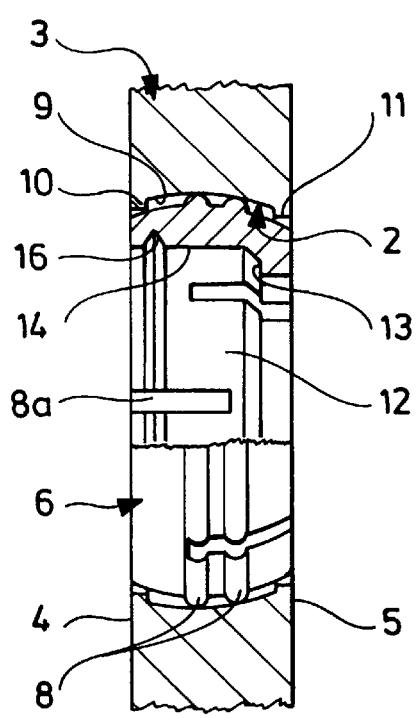
FIG. 4 is a view similar to FIG. 1 of a modified construction of a bearing ring without an inserted holding element.

It is also possible in the case of this embodiment to construct the bearing ring 6 to be elastically compressible through axis-parallel incisions 8 so that it can snap elastically into the opening 2 without it being necessary to perform a deformation of the material of the bone plate 3 in the region of the steps 10 or 11. FIG. 4 shows an axially compressible bearing ring 6 provided with incisions 8a in a corresponding manner.

The bearing ring 6 has a cylindrical passage 12 which narrows at one side in the form of a step 13. In the expanded section 14, an annular groove 16 with triangular cross-section is arranged in the wall 15 of the passage 12.

The bone screw 1 is inserted into the bearing ring 6. It has a shaft 17 with an external thread 18 as well as a head-shaped widened portion 19, which is cylindrical in the shown embodiment and fits exactly into the expanded section 14 of the passage 13. The widened portion 19 abuts against the step 13 of the bearing ring 6 with a rebounding shoulder 20 and thus restricts the insertion depth of the bone screw 1 into the bearing ring 6. When fully inserted, a circumferential rib 21 of complementary construction to the cross-sectional form of the annular groove 16 on the outside wall of the widened portion 19 engages into this annular groove 16 and thus secures the bone screw 1 against axial displacement relative to the bearing ring 6.

The bone screw 1 has a central stepped blind hole 22 which extends deep into the shaft 17. Radially extending incisions 23, which divide the widened portion into individual sector-shaped portions 24, are provided in the region of the widened portion 19. These portions 24 can be deformed elastically inwards into the blind hole 22 by this division, so that when the bone screw 1 is inserted into the bearing ring 6 the circumferential rib 21 can lock elastically into the annular groove 16.

In order to lock the bone screw 1 permanently in the bearing ring 6 in this locked position, a pin-shaped core 25, which is shorter overall than the blind hole 22, is inserted into the central blind hole 22. This core 25 comprises an upper section 26, the outside diameter of which corresponds to the inside diameter of the blind hole 22 in the region of the widened portion, and a lower section 27, which is formed by two axis-parallel arms separated from one another by an incision 28, said arms bearing an outwardly projecting catch 30 respectively at their free end. These catches 30 are triangular in cross-section with an upper stop surface 31 running transversely to the longitudinal direction of the core 25, a boundary surface 32 running in the direction of the arms 29 and a slide-on surface 33 sloping upwards from below and extending outwards.

An annular groove 34, also triangular in cross-section, into which the catches 30 can enter elastically when the core 25 is inserted into the blind hole 22 (FIG. 1), is worked into the blind hole 22. The dimensions in this case are selected so that when the catch 30 locks into the annular groove 34, the upper section 26 of the core 25 fills out the blind hole 22 in the region of the widened portion 19 and thus prevents elastic compression of the sections 24 of the widened portion 19. This position is referred to as the locking position.

The core 25 can be inserted deeper into the blind hole 22. A certain insertion force is necessary for this, since the core 25 is held in the locking position by the catches 30 locked into the annular groove 34. However, if this insertion force is overcome, the slide-on surfaces 33 slide along the edge of the annular groove 34 and lift the catches 30 out of the annular groove 34 upon elastic deformation of the arms 29. The core 25 can then be inserted into the blind hole 22 so deeply that the upper section 26 leaves the widened portion 19 and completely frees the blind hole 22 in the region of the widened portion 19. This position of the core (FIG. 3) is referred to as the release position. In this position, the sections 24 of the widened portion 19 can be bent elastically radially inwards so that it is possible to push the bone screw 1 out of the bearing ring 6, because the circumferential rib 21 can move out of the annular groove 16 by elastic bending of the sections 24.

The core 25 has an internal threaded bore 35 on its upper end into which a pulling member 36 may be screwed (FIG. 3), which can comprise a handle (not shown in the drawing). This pulling member 36 allows the core 25 to be drawn out of the release position and into the locking position again, whereby the catches 30 lock into the annular groove 34. Once the stop surfaces 34 abut against the corresponding end surface of the annular groove 34, a further displacement of the core 25 out of the blind hole 22 is no longer possible, i.e. the core 25 is mounted undetachably in the blind hole 22 and can only be displaced between the locking position and the release position.

In the embodiment shown in the drawing, the bone screw is mounted in the bearing ring. However, it goes without saying that the widened portion can also be mounted directly in the opening of a bone plate without such a bearing ring being interposed. In this case, the widened portion is preferably constructed in the form of a spherical ring and received in an appropriately shaped opening. So long as the widened portion can be elastically compressed, it can be inserted into this opening or removed from it. However, if the core 25 is located in the locking position, so this is no longer possible, the widened portion is then mounted so that it is not axially displaceable, but can be freely rotated and freely swivelled in the opening of the bone plate.

The bone screw is usually screwed into the bone by inserting a hexagon socket screw key or similar tool into the appropriately constructed blind hole 22. However, this is only possible so long as this blind hole 22 is not filled out by the core 25. In the locking position, the core 25 thus additionally forms a safeguard against a rotary tool being inserted into the bone screw when undesirable and rotating it. It is necessary to displace the core into the release position to permit handling of the bone screw. As a result, the core additionally performs a securing function besides the locking function.

What us claimed is:

1. A pin-type holding element for an orthopaedic holding system with an elastically compressible, head-shaped widened portion and with a central opening, into which a core may be inserted, which prevents an elastic compression of the head-shaped widened portion by filling out the central opening in the region of the widened portion without expansion, wherein:

the core is displaceable in the opening between a locking position, in which it fills out the central opening in the region of the widened portion, and a release position plunging deeper into the central opening, in which it releases the central opening in the region of the widened portion and thus allows its elastic compression.

2. A pin-type holding element according to claim 1, wherein:

the core can be fixed in the central opening in the locking position against a displacement along the central opening.

3. A pin-type holding element according to claim 2, wherein:

the core can be fixed in the locking position in the central opening by an elastic catch connection.

4. A pin-type holding element according to claim 3, wherein.

the catch connection can be released by overcoming a releasing force.

5. A pin-type holding element according to claim 4, wherein:

the catch connection can only be released in a direction towards being inserted more deeply.

6. A pin-type holding element according to claim 5, wherein:

the core bears a catch which may be pressed in elastically in a radial direction, and locks into a catch recess in a wall of the central opening.

7. A pin-type holding element according to claim 6, wherein;

the catch bears a slide-on surface on a side directed into the central opening.

8. A pin-type holding element according to claim 6, wherein:

the catch abuts against a stop, when the core is located in the locking position, so that the core cannot be removed from the holding element via the locking position.

9. A pin-type holding element according to claim 5, wherein:

the core bears catches which may be pressed in elastically in a radial direction, and lock into respective catch recesses in a wall of the central opening, and at a lower end of the core, two opposing elastic arms are arranged in extension of the core which bear the catches on respective free ends of the arms.

10. A pin-type holding element according to claim 6, wherein:

the catch is triangular in cross-section with a stop surface running transversely to the displacement direction on an upper end of the catch, an internal boundary running perpendicular thereto and with a slide-on surface directed radially outwards and sloping upwards from below.

11. A pin-type holding element according to claim 10, wherein:

the catch recess is triangular in cross-section with an upper stop surface running transversely to the longitudinal direction of the central opening, and with a lower boundary running parallel to the slide-on surface of the catch.

12. A pin-type holding element according to claim 6, wherein:

the catch recess is constructed as an annular groove in an inside wall of the central opening.

13. A pin-type holding element according to claim 1, wherein:

the core has a mounting for a pulling device on its upper side.

14. A pin-type holding element according to claim 13, wherein:

the mounting is constructed as an internal threaded bore.

15. A pin-type holding element according to claim 1, wherein:

the central opening is constructed as a blind hole.

16. A pin-type holding element according to claim 1, wherein:

the widened portion is held in a ring, which is mounted in an opening of a bone plate with an edge rebounding in a center with respect to an upper side and a lower side of the bone plate so that the ring is axially undetachable and may be freely rotated and swivelled, and that the edge of the opening is narrowed on the upper or on the lower side only after the ring is inserted into the opening by deformation in relation to the center of the opening.

* * * * *